United States Patent

Föry et al.

Patent Number: 5,407,900
Date of Patent: Apr. 18, 1995

[54] PYRIDYLSULFONYLUREAS

[75] Inventors: Werner Föry, Riehen; Rolf Schurter, Binningen, both of Switzerland

[73] Assignee: Ciba-Geigy Corporation, Ardsley, N.Y.

[21] Appl. No.: 96,137

[22] Filed: Jul. 22, 1993

[30] Foreign Application Priority Data

Jul. 30, 1992 [CH] Switzerland ............... 2402/92
Feb. 2, 1993 [CH] Switzerland ............... 313/93

[51] Int. Cl.$^6$ .............. C07D 401/12; A01N 43/66
[52] U.S. Cl. ............................. 504/213; 544/212
[58] Field of Search ........................ 544/212; 504/213

[56] References Cited

U.S. PATENT DOCUMENTS

| | | | |
|---|---|---|---|
| 4,515,626 | 5/1985 | Szczepanski | 73/93 |
| 4,544,401 | 10/1985 | Levitt | 71/92 |
| 4,546,179 | 10/1985 | Keinz | 544/206 |
| 4,579,583 | 4/1986 | Föry et al. | 71/92 |
| 4,600,428 | 7/1986 | Szczepanski | 71/76 |
| 4,670,559 | 6/1987 | Szczepanski | 544/211 |
| 4,690,707 | 9/1987 | Föry et al. | 71/93 |
| 4,759,791 | 7/1988 | Föry et al. | 71/91 |
| 4,778,889 | 10/1988 | Szczepanski | 544/211 |
| 4,854,963 | 8/1989 | Föry et al. | 71/91 |
| 4,881,964 | 1/1989 | Föry et al. | 71/91 |
| 4,891,443 | 1/1990 | Szczepanski | 564/103 |

FOREIGN PATENT DOCUMENTS

| | | |
|---|---|---|
| 030140 | 6/1981 | European Pat. Off. . |
| 103543 | 3/1984 | European Pat. Off. . |
| 108708 | 5/1984 | European Pat. Off. . |
| 0206995 | 12/1986 | European Pat. Off. . |
| 92/16522 | 10/1992 | WIPO . |

*Primary Examiner*—John M. Ford
*Attorney, Agent, or Firm*—George Dohmann; Marla J. Mathias

[57] ABSTRACT

(Cyclopropyl-triazinyl- and cyclopropyl-pyrimidinyl-)pyridylsulfonylureas of formula I

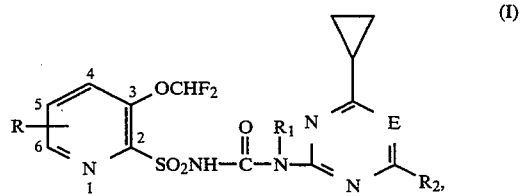

wherein
R and $R_1$ are each independently of the other hydrogen or methyl;
$R_2$ is methyl, methoxy or ethoxy; and
E is nitrogen or the methine group;

and the salts of those compounds, have good selective herbicidal properties. The preparation of those compounds and the use thereof as herbicidal active ingredients are described.

12 Claims, No Drawings

PYRIDYLSULFONYLUREAS

The present invention relates to novel, herbicidally active (cyclopropyl-triazinyl- and cyclopropyl-pyrimidinyl-)pyridylsulfonylureas, to processes for the preparation thereof, to compositions comprising those (cyclopropyl-triazinyl- and cyclopropyl-pyrimidinyl-)-pyridylsulfonylureas as active ingredients, and to the use thereof in controlling weeds, especially in crops of useful plants, for example cereals, cotton, soybeans, maize, rice and, more especially, rape.

N-Pyridinylsulfonyl-N'-pyrimidinyl- and N-pyridinylsulfonyl-N'-triazinyl-ureas having herbicidal action are already known and are described, for example, in EP-A-0 103 543 and U.S. Pat. No. 4 544 401.

Novel sulfonylureas having herbicidal properties have now been found.

The (cyclopropyl-triazinyl- and cyclopropyl-pyrimidinyl-)pyridylsulfonylureas according to the invention have the formula I

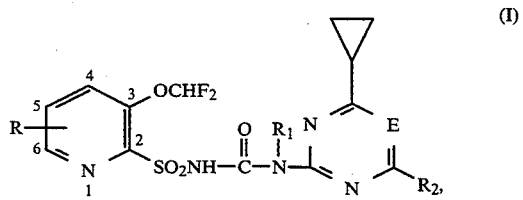

wherein
R and $R_1$ are each independently of the other hydrogen or methyl;
$R_2$ is methyl, methoxy or ethoxy; and
E is nitrogen or the methine group;
and the agrochemically acceptable salts of those compounds.

The invention also covers the salts which the compounds of formula I, being sulfonamides with an acidic proton, may form with amines, alkali metal and alkaline earth metal bases or quaternary ammonium bases.

Examples of amines suitable for salt formation are primary, secondary and tertiary aliphatic and aromatic amines, such as methylamine, ethylamine, nopropylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methylhexylamine, methyl-nonylamine, methyl-pentadecylamine, methyl-octadecylamine, ethyl-butylamine, ethyl-heptylamine, ethyl-octylarriine, hexyl-heptylamine, hexyl-octylamine, dimethylamine, diethylamine, di-n-propylamine, diisopropylamine, di-n-butylamine, di-n-amylamine, diisoamylamine, dihexylaraine, diheptylamine, dioctylamine, ethanolamine, n-propanolamine, isopropanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, diethanolamine, trimethylamine, triethylamine, tri-n-propylamine, triisopropylamine, tri-n-butylamine, triisobutylamine, tri-sec-butylamine, tri-n-amylamine; heterocyclic amines, for example pyridine, quinoline, isoquinoline, morpholine, N-methylmorpholine, thiomorpholine, piperidine, pyrrolidine, indoline, quinuclidine and azepine; primary arylamines, for example anilines, methoxyanilines, ethoxyanilines, o,m,p-toluidines, phenylenediamines, benzidines, naphthylamines and o,m,p-chloroanilines; but especially ethyl-, propyl-, diethyl- or triethyl-amine, and more especially isopropylamine and diethanolamine.

Examples of quaternary ammonium bases are generally the cations of ammonium halides, for example the tetramethylammonium cation, the trimethylbenzylammonium cation, the triethylbenzylammonium cation, the tetraethylammonium cation and the trimethylethylammonium cation, and also the ammonium cation.

Alkali metal and alkaline earth metal bases as salt formers that should be given special mention are the hydroxides of lithium, magnesium or calcium, especially of sodium or potassium.

The compounds of formula I wherein E is the methine group are preferred.

Preference is also given to compounds of formula $I_a$

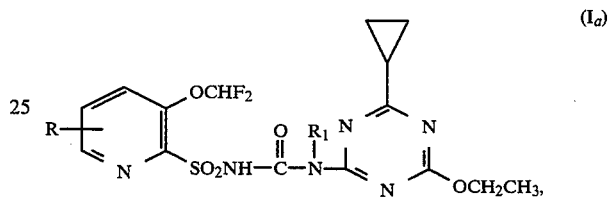

wherein R and $R_1$ are as defined above.

Also preferred are compounds of formula I wherein R is bonded in the 6-position.

Special preference is given to the compound of formula $I_b$

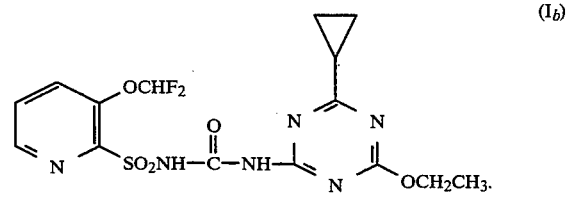

The compounds of formula I can be prepared by
a) reacting a 2-pyridylsulfonamide of formula II

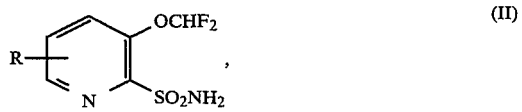

wherein R is as defined, with an N-2-pyrimidinyl- or N-2-triazinyl-carbamate of formula III

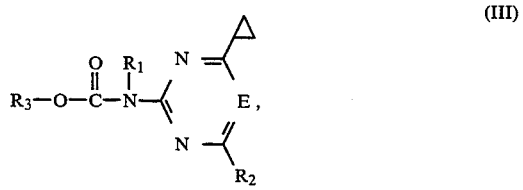

wherein $R_1$, $R_2$ and E are as defined for formula I and $R_3$ is phenyl or 4-tolyl, in the presence of a base, or
b) reacting a 2-pyridylsulfonamide of formula IV

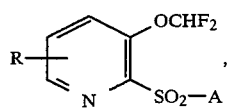 (IV)

wherein R is as defined and A is wherein R₃ is as defined above, optionally in the presence of a base, with a 2-aminopyrimidine or 2-aminotriazine of formula V

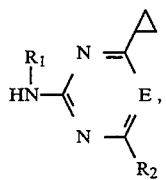 (V)

wherein $R_1$, $R_2$ and E are as defined, or c) reacting a 2-pyridylsulfonyl chloride of formula VI

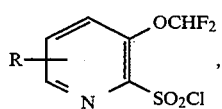 (VI)

wherein R is as defined, with a metal cyanate of formula VII $$O=C=N^{\ominus}M^{\oplus} \quad \text{(VII)},$$

wherein $M^{\oplus}$ is an ammonium, phosphonium, sulfonium or alkali metal cation, and with a 2-aminopyrimidine or 2-aminotriazine of formula Va

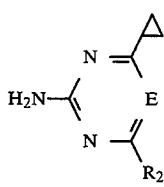 (Va)

wherein $R_2$ and E are as defined, optionally in the presence of a base in an inert, organic solvent, or d) reacting a 2-pyridylsulfonamide of formula II

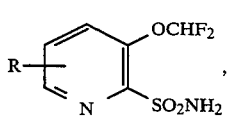 (II)

wherein R is as defined, optionally in the presence of a base, with a 2-pyrimidinyl- or 2-triazinyl-isocyanate of formula VIII

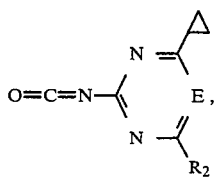 (VIII)

wherein $R_2$ and E are as defined.

Process variants a), b), c) and d) follow reaction scheme 1.

Reaction scheme 1:

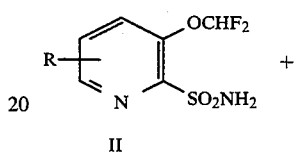

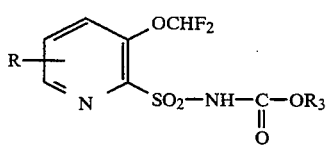

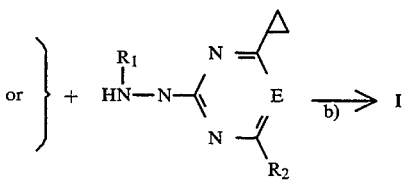

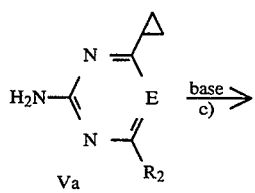

Reaction scheme 1:
-continued

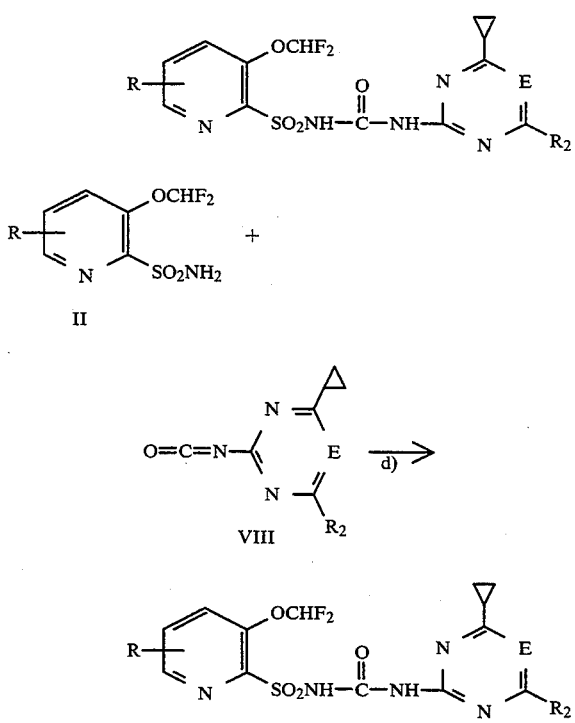

The reactions to form compounds of formula I in accordance with process variants a) to d) are advantageously carried out in aprotic, inert, organic solvents. Such solvents are hydrocarbons, such as benzene, toluene, xylene, hexane or cyclohexane, chlorinated hydrocarbons, such as dichloromethane, trichloromethane, tetrachloromethane or chlorobenzene, ethers, such as diethyl ether, ethylene glycol dimethyl ether, diethylene glycol dimethyl ether, tetrahydrofuran or dioxane, nitriles, such as acetonitrile and propionitrile, amides, such as dimethylformamide, diethylformamide or N-methylpyrrolidone, and esters, such as ethyl acetate. The reaction temperatures are preferably from 0° C. to +150° C.

Generally the reactions are not exothermic or are only slightly exothermic and can be carried out at temperatures of from +20° C. to +60° C. In order to reduce the reaction time or in order to initiate the reaction it is advantageous to heat the reaction mixture to boiling point for a short time. The reaction times can also be reduced by the addition of either catalytic amounts or up to 2 equivalents of a base as reaction catalyst. Suitable bases are especially tertiary amines, such as trimethylamine, triethylamine, quinuclidine, 1,4-diazabicyclo(2.2.2)octane, 1,5-diazabicyclo(4.3.0)non-5-ene or 1,5-diazabicyclo(5.4.0)undec-5-ene or pyridine and 4-(N,N-dimethylamino)-pyridine. It is also possible, however, to use as bases inorganic bases, such as hydrides, for example sodium or calcium hydride, hydroxides, for example sodium and potassium hydroxide, carbonates, for example sodium and potassium carbonate, or hydrogen carbonates, for example potassium and sodium hydrogen carbonate.

The end products of formula I can be isolated by concentration and/or evaporation of the solvent and purified by recrystallisation or trituration of the solid residue in solvents in which they are not readily soluble, for example dilute aqueous acid, such as 2N hydrochloric acid, ethers, esters, aromatic hydrocarbons or chlorinated hydrocarbons.

Another possible method of isolating and purifying the products of formula I is (flash) chromatography on silica gel using a suitable solvent or solvent mixture, for example ethyl acetate, hexane or tetrahydrofuran.

The starting compounds of formulae II, III, IV, V, Va, VI, VII and VIII required for the preparation processes are either known or can be prepared from known compounds analogously to known processes. Processes for the preparation of 2-pyridylsulfonamides of formula II are described, for example, in EP-A-0 103 543. The intermediates of formula IV can be prepared from the corresponding sulfonamides of formula II analogously to known processes. Such reactions are described, for example, in EP-A-0 103 543. Processes for the preparation of the intermediates of formulae III, V, Va and VIII are described, for example, in EP-A-0 108 708.

The compounds of formula I may be used in unmodified form, that is to say as obtainable from the synthesis, but they are preferably formulated in customary manner together with the adjuvants customarily employed in formulation technology e.g. into emulsifiable concentrates, directly sprayable or dilutable solutions, dilute emulsions, wettable powders, soluble powders, dusts, granules or microcapsules. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the compound (active ingredient) of formula I and, where appropriate, one or more solid or liquid adjuvants, are prepared in known manner, e.g. by homogeneously mixing and/or grinding the active ingredients with the adjuvants, e.g. solvents or solid carriers. It is also possible to use surface-active compounds (surfactants) in the preparation of the formulations.

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons, such as paraffins, cyclohexane or tetrahydronaphthalene; alcohols, such as ethanol, propanol or butanol; glycols and their ethers and esters, such as propylene glycol or dipropylene glycol ether; ketones, such as cyclohexanone, isophorone or diacetone alcohol; strongly polar solvents, such as N-methyl-2-pyrrolidone, dimethyl sulfoxide or water; vegetable oils and esters thereof, such as rape oil, castor oil or soybean oil; and, where appropriate, also silicone oils.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonire; and suitable nonsorbent carriers are, for example, calcite or sand. In addition, a great number of pregranulated materials of inorganic or organic nature can be used, e.g. especially dolomite or pulverised plant residues.

Depending upon the nature of the compound of formula I to be formulated, suitable surface-active compounds are non-ionic, cationic and/or anionic surfactants having good emulsifying, dispersing and wetting properties. The term "surfactants" will also be understood as comprising mixtures of suffactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$-$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltdmethylammonium chloride or benzyldi(2-chloroethyl)ethylammonium bromide.

The surfactants customarily employed in formulation technology, which may also be used in the compositions according to the invention, are described inter alia in the following publications:

"Mc Cutcheon's Detergents and Emulsifiers Annual", Mc Publishing Corp., Glen Rock, N.J., 1988.

M. and J. Ash, "Encyclopedia of Surfactants", Vol. I–III, Chemical Publishing Co., New York, 1980–1981.

Dr. Helmut Stache "Tensid-Taschenbuch" (Surfactant Handbook), Carl Hanser Verlag, Munich/Vienna 1981.

The herbicidal compositions usually comprise 0.1 to 99%, preferably 0.1 to 95%, of a compound of formula I, 1 to 99% of a solid or liquid adjuvant, and 0 to 25%, preferably 0.1 to 25%, of a surfactant.

Whereas commercial products will preferably be formulated as concentrates, the end user will normally employ dilute formulations.

The compositions may also comprise further auxiliaries, such as stabilisers, e.g. vegetable oils or epoxidised vegetable oils (epoxidised coconut oil, rape oil or soybean oil), antifoams, e.g. silicone oil, preservatives, viscosity regulators, binders and tackifiers, as well as fertilisers or other active ingredients for obtaining special effects.

Preferred formulations have especially the following composition (throughout, percentages are by weight):

| Emulsifiable concentrates: | | |
|---|---|---|
| active ingredient: | 1 to 90%, | preferably 5 to 50% |
| surface-active anent: | 5 to 30%, | preferably 10 to 20% |
| solvent: | 15 to 94%, | preferably 70 to 85% |
| Dusts: | | |
| active ingredient: | 0.1 to 50%, | preferably 0.1 to 5% |
| solid carrier: | 99.9 to 90%, | preferably 99.9 to 99% |
| Suspension concentrates: | | |
| active ingredient: | 5 to 75%, | preferably 10 to 50% |
| water: | 94 to 24%, | preferably 88 to 30% |
| surface-active agent: | 1 to 40%, | preferably 2 to 30% |
| Wettable powders: | | |
| active ingredient: | 0.5 to 90%, | preferably 1 to 80% |
| surface-active agent: | 0.5 to 20%, | preferably 1 to 15% |
| solid carrier: | 5 to 95%, | preferably 15 to 90% |
| Granules: | | |
| active ingredient: | 0.1 to 30%, | preferably 0.1 to 15% |
| solid carrier: | 99.5 to 70%, | preferably 97 to 85% |

The compounds of formula I are generally used successfully at rates of application of from 0.001 to 2 kg/ha, especially from 0.005 to 1 kg/ha.

The concentration required to achieve the desired effect can be determined by experiment. It is dependent upon the type of action, the stage of development of the cultivated plant and of the weed, and also upon the application (place, time, method) and, in dependence on those parameters, can vary within wide limits.

When used at relatively low rates of application, the compounds of formula I are distinguished by growth-inhibiting and herbicidal properties which render them excellently suitable for use in crops of useful plants, especially in cereals, cotton, soybeans, maize and rice, special preference being given to use in rape crops.

The following Examples further illustrate the invention but do not limit the invention.

PREPARATION EXAMPLE

Example P1

Preparation of N-(3-Difluoromethoxypyridine-2-Sulfonyl)-N'-(4-Cyclopropyl-6-Ethoxy-Triazin-2-yl)-Urea (Comp. No. 1.001)

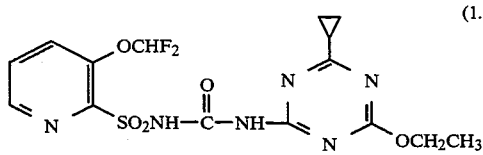
(1.001)

1.63 ml of 1,5-diazabicyclo(5.4.0)undec-5-ene followed by 3.15 g of N-(4-cyclopropyl-6-ethoxy-triazin-2-yl)-phenylcarbamate are added to a solution of 2.24 g of 3-difluoromethoxypyridin-2-yl-sulfonamide in 40 ml of acetonitrile. The reaction mixture is stirred for 45 minutes at room temperature and then concentrated using a rotary evaporator. The oily residue is triturated with 8 ml of 2N hydrochloric acid and diluted with 10 ml of water. The crystal mass is filtered off, washed with water and diethyl ether and dried, yielding 4.05 g of N-(3-difluoromethoxypyridine-2-sulfonyl)-N'-(4-cyclopropyl-6-ethoxy-triazin-2-yl)-urea having a melting point of 144°–145° C.

The compounds of formula I listed in Table 1 below are prepared in analogous manner.

TABLE 1

Compounds of formula I

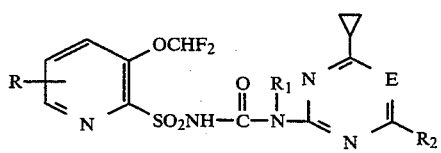
(I)

| Comp. No. | R | $R_1$ | $R_2$ | E | Phys.-chem. data |
|---|---|---|---|---|---|
| 1.001 | H | H | $OC_2H_5$ | N | m.p. 144–145° C. |
| 1.002 | 6-$CH_3$ | H | $OC_2H_5$ | N | m.p. 152–153° C. (decomp.) |
| 1.003 | H | $CH_3$ | $OC_2H_5$ | N | |
| 1.004 | H | H | $OCH_3$ | N | m.p. 146–149° C. |
| 1.005 | H | H | $OCH_3$ | CH | |
| 1.006 | H | H | $CH_3$ | CH | m.p. 137–139° C. |
| 1.007 | 6-$CH_3$ | H | $CH_3$ | CH | |

Formulation Examples for active ingredients of formula I (throughout, percentages are by weight)

| F1. Emulsifiable concentrates | a) | b) | c) | d) |
|---|---|---|---|---|
| a compound of Table 1 | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |
| cyclohexanone | — | — | 10% | 20% |
| aromatic hydrocarbon mixture $C_9$–$C_{12}$ | 85% | 78% | 55% | 16% |

Emulsions of any required concentration can be obtained from such concentrates by dilution with water.

| F2. Solutions | a) | b) | c) | d) |
|---|---|---|---|---|
| a compound of Table 1 | 5% | 10% | 50% | 90% |
| dipropylene glycol methyl ether | — | 20% | 20% | — |
| polyethylene glycol (mol. wt. 400) | 20% | 10% | — | — |
| N-methyl-2-pyrrolidone | — | — | 30% | 10% |
| aromatic hydrocarbon mixture $C_9$–$C_{12}$ | 75% | 60% | — | — |

These solutions are suitable for application in the form of microdrops.

| F3. Wettable powders | a) | b) | c) | d) |
|---|---|---|---|---|
| a compound of Table 1 | 1% | 5% | 25% | 50% |
| sodium lignosulfonate | 3% | 4% | — | 3% |
| sodium laurylsulfate | — | — | 3% | 1% |
| sodium diisobutylnaphthalene-sulfonate | — | 3% | 6% | 5% |
| octylphenol polyglycol ether (7–8 mol of ethylene oxide) | 2% | 1% | — | — |
| highly dispersed silicic acid | 2% | 2% | 5% | 5% |
| kaolin | 42% | 35% | 61% | 36% |
| sodium chloride | 50% | 50% | — | — |

The active ingredient is thoroughly mixed with the adjuvants and the mixture is thoroughly ground in a suitable mill, affording wettable powders which can be diluted with water to give suspensions of the desired concentration.

| F4. Coated granules | a) | b) | c) |
|---|---|---|---|
| a compound of Table 1 | 0.1% | 5% | 15% |
| highly dispersed silicic acid | 0.9% | 2% | 2% |
| inorganic carrier (diameter 0.1–1 mm) for example $CaCO_3$ or $SiO_2$ | 99.0% | 93% | 83% |

The active ingredient is dissolved in methylene chloride and sprayed onto the carrier, and the solvent is then evaporated off in vacuo.

| F5. Coated granules | a) | b) | c) |
|---|---|---|---|
| a compound of Table 1 | 0.1% | 5% | 15% |
| polyethylene glycol (mol. wt. 200) | 1.0% | 2% | 3% |
| highly dispersed silicic acid | 0.9% | 1% | 2% |
| inorganic carrier (diameter 0.1–1 mm) for example $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| a compound of Table 1 | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c |
|---|---|---|---|
| a compound of Table 1 | 0.1% | 1% | 5% |

-continued

| F7. Dusts | a) | b) | c |
|---|---|---|---|
| talcum | 39.9% | 49% | 35% |
| kaolin | 60.0% | 50% | 60% |

Ready-for-use dusts are obtained by mixing the active ingredient with the carders and grinding the mixture in a suitable mill.

| F8. Suspension concentrates | a) | b) | c) | d) |
|---|---|---|---|---|
| a compound of Table 1 | 3% | 10% | 25% | 50% |
| ethylene glycol | 5% | 5% | 5% | 5% |
| nonylphenol polyglycol ether (15 mol of ethylene oxide) | — | 1% | 2% | 1% |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

BIOLOGICAL EXAMPLES

Example B1

Pre-Emergence Herbicidal Action

Plastic pots are filled with expanded vermiculite (density: 0.135 g/cm³, water-adsorption capacity: 565 g/l). After the non-adsorptive vermiculite has been saturated with an aqueous emulsion in deionised water, prepared from a 25 % wettable powder formulation (Example F3 c)), comprising the active ingredients in a concentration of 70 ppm, seeds of the following plants are sown on the surface: *Nasturtium officinalis, Agrostis tenuis, Stellaria media* and *Digitaria sanguinalis*. The pots are then kept in a climatic chamber at a temperature of 20° C., illumination of about 20 klux and 70% relative humidity. During the germination phase of 4 to 5 days the pots are covered with light-permeable material and watered with deionised water in order to increase the local humidity. After the 5th day, 0.5% of a commercial liquid fertiliser is added to the water. The test is evaluated 12 days after sowing and the action on the test plants is assessed in accordance with the following scale:

| 1 | plant has not germinated or has withered |
|---|---|
| 2-3 | very pronounced phytotoxic action |
| 4-6 | medium action |
| 7-8 | weak action |
| 9 | no action, the plant is growing as untreated controls |

The test compounds of Table 1 exhibit pronounced herbicidal action in this test.

Examples of the good herbicidal action are given in Table B1:

TABLE B1

| | | Pre-emergence action | | |
|---|---|---|---|---|
| | | Test plants: | | |
| Comp. No. | Conc. [μg/leaf] | Nasturtium | Agrostis | Stellaria | Digitaria |
| 1.001 | 100 | 3 | 2 | 3 | 3 |
| 1.002 | 100 | 3 | 5 | 3 | 5 |

TABLE B1-continued

| | | Pre-emergence action | | |
|---|---|---|---|---|
| | | Test plants: | | |
| Comp. No. | Conc. [μg/leaf] | Nasturtium | Agrostis | Stellaria | Digitaria |
| 1.004 | 100 | 3 | 2 | 2 | 2 |

The same results are obtained when the compounds of formula I are formulated in accordance with Examples F1, F2 and F4 to F8.

Example B2

Post-Emergence Herbicidal Action (Contact Herbicide)

Monocotyledonous and dicotyledonous test plants are raised in a greenhouse in plastic pots containing standard soil and in the 4- to 6-leaf stage are sprayed with an aqueous suspension of the test compounds of Table 1, prepared from a 25 % wettable powder formulation (Example F3 b)) corresponding to a rate of application of 8 to 500 g of active ingredient per hectare (500 l of water/ha). The test plants are then grown in the greenhouse under optimum conditions. After about 18 days the test is evaluated in accordance with a scale of nine ratings (1=total damage, 9=no action). Ratings of 1 to 4 (especially 1 to 3) indicate good to very good herbicidal action.

The test compounds of Table 1 exhibit pronounced herbicidal action in this test.

The same results are obtained when the compounds of formula I are formulated in accordance with Examples F1, F2 and F4 to F8.

What is claimed is:

1. A compound of formula I

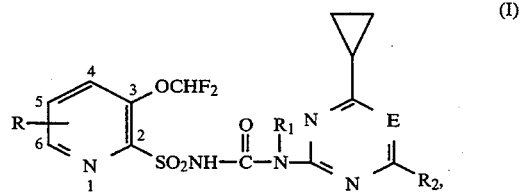

wherein

R and $R_1$ are each independently of the other hydrogen or methyl;

$R_2$ is methyl, methoxy or ethoxy; and

E is nitrogen or an agrochemically acceptable salt of such a compound.

2. A compound according to claim 1 of formula $I_a$

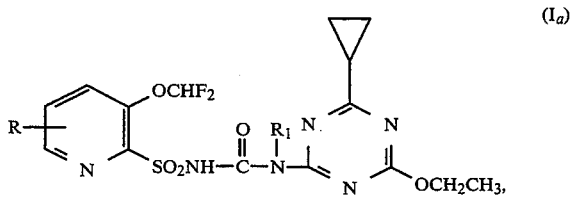

wherein R and $R_1$ are as defined in claim 1.

3. A compound according to claim 1 of formula I wherein R is bonded in the 6-position.

4. A compound according to claim 1 of formula $I_b$

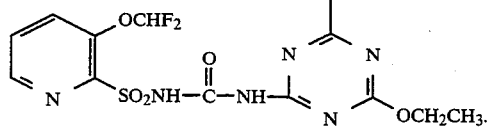
(I_b)

5. A herbicidal composition comprising a compound of formula I according to claim 1, and an inert carrier.

6. A composition according to claim 5 comprising from 0.1% to 95% of a compound of formula I, from 1 to 99% of a solid or liquid adjuvant and from 0 to 25% of a surfactant.

7. A method of controlling undesirable plant growth, which method comprises applying a compound of formula I according to claim 1 in an effective amount to the plants or to the locus thereof.

8. A method according to claim 7, wherein said compound is applied in an amount of from 0.001 to 2 kg per hectare.

9. A method according to claim 7 for the selective pre- or post-emergence control of weeds in crops of useful plants.

10. A composition according to claim 6, wherein the surfactant is present in an amount from 0.1 to 25%.

11. A method of controlling undesirable plant growth, which method comprises applying a composition according to claim 5 in an effective amount to the plants or to the locus thereof.

12. A method according to claim 7, wherein the useful plants are selected from the group consisting of cereals, cotton, soybeans, maize, rice and rape.

* * * * *